US008883011B2

(12) United States Patent
Lubda et al.

(10) Patent No.: US 8,883,011 B2
(45) Date of Patent: Nov. 11, 2014

(54) PRODUCTION OF MONOLITHIC SEPARATING COLUMNS

(75) Inventors: Dieter Lubda, Bensheim (DE); Karin Cabrera Perez, Dreieich (DE); Klaus Kreher, Muenster (DE); Charles Roderick McIlwrick, Fuerth/Odenwald (DE)

(73) Assignee: Merck Patent GmbH, Darmstadt (DE)

( * ) Notice: Subject to any disclaimer, the term of this patent is extended or adjusted under 35 U.S.C. 154(b) by 1037 days.

(21) Appl. No.: 11/783,286

(22) Filed: Apr. 6, 2007

(65) Prior Publication Data

US 2009/0101580 A1 Apr. 23, 2009

(30) Foreign Application Priority Data

Apr. 7, 2006 (EP) .................................... 06007395
Apr. 20, 2006 (EP) .................................... 06008141

(51) Int. Cl.
*B01D 15/22* (2006.01)
*B01J 20/285* (2006.01)
*B01J 20/283* (2006.01)
*B01J 20/30* (2006.01)
*B01J 20/282* (2006.01)
*B01J 20/28* (2006.01)
*B24B 5/22* (2006.01)
*B01J 20/284* (2006.01)
*G01N 30/52* (2006.01)
*G01N 30/60* (2006.01)

(52) U.S. Cl.
CPC ................ *B24B 5/22* (2013.01); *B01J 20/285* (2013.01); *G01N 2030/528* (2013.01); *B01D 15/22* (2013.01); *B01J 20/283* (2013.01); *B01J 2220/82* (2013.01); *B01J 20/3021* (2013.01); *B01J 20/282* (2013.01); *G01N 30/6052* (2013.01); *B01J 20/28042* (2013.01); *B01J 20/284* (2013.01)
USPC ........ 210/656; 210/635; 210/198.2; 210/502.1

(58) Field of Classification Search
CPC .. B01J 20/28042; B01J 20/282; B01J 20/283; B01J 20/3021; B01J 20/285; B01J 2220/82; B24B 5/22; B01D 15/22; G01N 2030/528; G01N 30/6052
USPC .................... 210/656, 635, 659, 198.2, 502.1
See application file for complete search history.

(56) References Cited

U.S. PATENT DOCUMENTS 1,809,880 A * 6/1931 Wise ................................. 72/70
2,194,488 A * 3/1940 Whitehouse ................... 264/291

(Continued)

FOREIGN PATENT DOCUMENTS

| DE | 19946674 A1 | 4/2001 |
| EP | 0363697 | 4/1990 |

(Continued)

OTHER PUBLICATIONS

F. Svec und J. M. Freshet (1992) Anal. Chem. 64, Seiten 820-822.

(Continued)

*Primary Examiner* — Ernest G Therkorn
(74) *Attorney, Agent, or Firm* — Millen, White, Zelano & Branigan P.C.

(57) ABSTRACT

The present invention relates to a process for the production of monolithic separating columns using monolithic moldings whose diameter is reduced by grinding, and to separating columns having improved separation efficiency produced in this way, and to the use thereof.

20 Claims, 2 Drawing Sheets

(56) References Cited

U.S. PATENT DOCUMENTS

| | | | |
|---|---|---|---|
| 3,470,051 A * | 9/1969 | Meyer | 156/171 |
| 3,531,886 A * | 10/1970 | Vartanian et al. | 42/69.01 |
| 4,017,528 A | 4/1977 | Unger et al. | |
| 4,711,525 A * | 12/1987 | Feth | 385/11 |
| 4,862,836 A * | 9/1989 | Chen et al. | 123/3 |
| 5,009,688 A | 4/1991 | Nakanishi | |
| 5,047,438 A | 9/1991 | Feibush | |
| 5,194,207 A * | 3/1993 | Tokuda et al. | 264/129 |
| 5,624,875 A | 4/1997 | Nakanishi et al. | |
| 5,770,060 A * | 6/1998 | Ladisch et al. | 210/198.2 |
| 5,858,296 A | 1/1999 | Domb et al. | |
| 6,207,098 B1 | 3/2001 | Nakanishi et al. | |
| 6,291,216 B1 | 9/2001 | Muller et al. | |
| 7,250,214 B2 | 7/2007 | Walter et al. | |
| 2001/0031839 A1 | 10/2001 | Muller et al. | |
| 2002/0088753 A1 | 7/2002 | Huber et al. | |
| 2003/0098279 A1 | 5/2003 | Cabrera et al. | |
| 2003/0155676 A1* | 8/2003 | Lubda et al. | 264/41 |
| 2003/0213732 A1 | 11/2003 | Malik et al. | |
| 2004/0000522 A1* | 1/2004 | Xie et al. | 210/656 |
| 2007/0012627 A1 | 1/2007 | Ivanov et al. | |
| 2007/0135304 A1 | 6/2007 | Walter et al. | |
| 2008/0032116 A1 | 2/2008 | Hosoya et al. | |
| 2009/0062522 A1* | 3/2009 | Erbacher et al. | 536/25.41 |

FOREIGN PATENT DOCUMENTS

| | | |
|---|---|---|
| EP | 0366252 A | 5/1990 |
| EP | 0710219 B1 | 12/1997 |
| EP | 1269179 A1 | 1/2003 |
| JP | 8 91957 | 4/1996 |
| JP | 2002 505005 | 2/2002 |
| JP | 2004 538468 | 12/2004 |
| WO | WO 94/19687 | 9/1994 |
| WO | WO 95/03256 | 2/1995 |
| WO | WO 95/10354 | 4/1995 |
| WO | WO 96/22316 | 7/1996 |
| WO | WO 98/29350 | 7/1998 |
| WO | WO 98/59238 | 12/1998 |
| WO | WO 01/03797 | 1/2001 |
| WO | WO 01/55713 | 8/2001 |
| WO | WO 01/58562 | 8/2001 |
| WO | WO 01/77660 | 10/2001 |
| WO | WO 03/014450 | 2/2003 |
| WO | WO 2004/064974 | 8/2004 |
| WO | WO 2005/116095 | 12/2005 |

OTHER PUBLICATIONS

S. Hjerten et al. (1989) J. Chromatogr. 473, Seiten 273-275.

XP004360281 Journal of Chromatography A, 959 (2002) 121-129, Lubbad S et al.

"Halterung fur monolithische Sorbentien," Espacenet, Publication Date: Feb. 12, 2002; English Abstract of JP-2002 505005.

Kikusui Kagaku Kogyo KK, "Method for processing porous ceramic and product therefrom," Espacenet, Publication Date: Apr. 9, 1996; English Abstract of JP-8 91957.

* cited by examiner

PRODUCTION OF MONOLITHIC SEPARATING COLUMNS

The present invention relates to a process for the production of monolithic separating columns using monolithic moldings whose diameter is reduced by grinding, and to separating columns having improved separation efficiency produced in this way and to the use thereof.

The development of miniaturised synthesis devices, in which chemical reactions can be carried out with extremely small amounts of starting material, has meant that the requirements made of the corresponding analysis devices have also increased in order to facilitate the separation of extremely small amounts of substance.

An important advantage of separating columns of relatively small diameter is the possibility of being able to detect significantly smaller amounts of substance. A separating column having a diameter of 3 mm has a detection sensitivity which is greater by a factor of 2.35 compared with a conventional column having a diameter of 4.6 mm (calculated from $F=(4.6/3)^2$).

Separating columns having a smaller diameter than the standard products (internal diameter 4.6 mm) are therefore being employed ever more frequently in chromatographic separation technology. Even in combination with the devices usually employed, however, the use of columns of smaller diameter has advantages since it requires smaller amounts of solvent. This also enables the use thereof in combination with mass-selective detection (LC/MS) without the need to split some of the mobile phase out before entry into the MS detector.

Due to their high permeability at the same time as high separation efficiency, monolithic separating columns can be employed for chromatographic separations with increased flow rates. This is an important advantage of the use of monolithic separating columns compared with other separating columns. On use of separating columns of smaller diameter, even greater detection sensitivities can additionally be achieved.

Various processes are known for the preparation of inorganic porous materials in the form of monolithic separating columns, in particular of corresponding columns based on silica gels. As also described in EP 0 710219 B1 or WO 98/29350, the sol-gel process is preferably used. The sol-gel method is the term applied to widespread methods in which firstly polymerizable low-molecular-weight species are generated and finally aggregated or polymerized materials are obtained via polymerization reactions. The sol-gel method is suitable, inter alia, for use in the hydrolysis of metal alkoxides, metal chlorides, metal salts or combination compounds, which generally contain carboxyl or beta-diketone ligands. A corresponding process is also described in EP 0 363 697, in which the solution of a metal alkoxide is subjected to a hydrolysis process together with an organic polymer as pore former. The subsequent polycondensation results ultimately in phase separation with a silicate-rich phase and an aqueous organic phase comprising the dissolved polymer. The materials prepared by this process are distinguished by interconnected open pores having a narrow pore-size distribution.

In order to produce a monolithic separating column by the sol-gel process, a sol is introduced into a mold, for example a tube, made from a suitable material having an internal diameter of, for example, 6 mm. This determines the later diameter of the resultant monolith which arises due to shrinkage. Experience shows that the shrinkage is about 15% of the original diameter.

It has now been found that, in the production of monoliths of smaller diameter, in particular diameters of less than about 5 mm, the sol-gel process described above results in products which do not have optimum chromatographic separation efficiencies.

Besides the inorganic monolithic chromatography columns, organic monolithic columns have become established to an ever-increasing extent in recent years since they have, under certain conditions, better properties than the inorganic separating columns usually employed. The organic monolithic columns are preferably highly crosslinked, hard organic polymer gels. In their preparation, these materials are also typically polymerized into molds, such as, for example, tubes. Processes for the preparation of organic monolithic polymers are known to the person skilled in the art. The preparation can be carried out, for example, in a similar manner to that in F. Svec and J. M. Frechet (1992) Anal. Chem. 64, pages 820-822, and S. Hjerten et al. (1989) J. Chromatogr. 473, pages 273-275, or WO 2005116095. Another possibility for the production of organic monolithic moldings is the production of an organic, polymeric cast of an inorganic porous molding, which is dissolved out after polymerization of the organic monomers. Corresponding processes are described in the patent applications EP 0 366 252 A and DE 199 46 674 A1.

An object of the present invention is therefore to provide separating columns which enable even small amounts of product mixture to be separated by chromatography with maximum sensitivity. However, a further object of the present invention is to provide separating columns, in particular of smaller diameter, which enable separations to be carried out with greater sensitivity, enabling even extremely small impurities to be detected better or at all.

In addition, it is desirable to produce improved separating columns which enable chromatographic separation to be coupled to mass spectrometry as detection technique and to be carried out in a single unit since these two methods complement one another very well. Since mass spectrometry instruments can generally be operated with only low flow rates, it is desirable to provide through the present invention separating columns of small diameter which can be combined with these instruments and, in spite of the smaller diameter, result in improved separation.

An object of the present invention is therefore to provide an inexpensive, simple-to-carry-out process for the production of monolithic separating columns which gives separating columns which have homogeneous properties over the entire column cross section, so that as far as possible the same separation efficiency is achieved in each volume element of the columns produced.

The object is achieved by a process in which, in a first step, monolithic moldings are provided, which are freed from the outer, inhomogeneous layer in the subsequent step by grinding. For this purpose, thin layers having a thickness of a few microns are ground off from the outside. It may be sufficient, in order to improve the properties, for the diameter of the moldings to be reduced by 5 µm by the grinding. The diameter is usually reduced to the desired extent, but at least by ≥20 µm, by a grinding step.

The reason why, in particular, monolithic chromatography columns of relatively small diameter frequently do not exhibit optimal separation efficiencies appears to lie in the increasing influence of the peripheral region of the monolith.

In the case of silica monoliths, domains of compacted silica gel, which may have an increased adverse effect on the separation result on reduction of the diameter, occur, for example, in the peripheral region.

As investigations have shown, the peripheral regions have a different structure to the volume elements of the monolith formed which lie further to the inside. While a three-dimensional network builds up in the interior, compacted domains of silica gel of significantly reduced porosity are evident in the peripheral region, which has an effect on the separation efficiency and peak symmetry. By means of SEM photomicrographs, it has been possible to show that the outer silica-gel layer of the monolithic column has an inhomogeneous structure. Contact of the sol with the inside surface of the gelling tube produces a different silica-gel structure than in the interior of the column. Domains form on the outer surface with an extremely dense silica-gel layer which does not exhibit the classical pore structure as in the interior of the monolith.

Surprisingly, it has been found that it is possible to produce corresponding columns of reduced diameter, for example of 3 or 2 mm or less, from monolithic moldings produced by conventional processes in gelling molds by grinding off the outer material, i.e. the outer cladding layer of the molding, in a suitable grinding process. This can be either a centreless grinding process or another process in which thin outer layers can be removed, preferably stepwise, from the respective monolithic molding under conditions matched to the sensitive material.

The present object is therefore achieved by preferably repeated, stepwise grinding-off of typically about 0.01 to 0.2 mm layers of the molding to the desired diameter.

In one aspect, the present invention relates to a process for the production of monolithic separating columns by
a) provision of a porous monolithic molding which has inhomogeneous peripheral regions
b) reduction in the diameter of the molding by at least 20 μm by grinding off the outer cladding layer one or more times.

The process according to the invention is particularly suitable for porous monolithic moldings produced in a gelling mold.

In a preferred embodiment, the ground molding is clad in a liquid-tight manner in a step c) following step b).

In a preferred embodiment, the diameter of the molding is reduced in step b) in a centreless grinding process.

In another preferred embodiment, the diameter of the molding is reduced in step b) with the aid of rotating grinding wheels.

In another preferred embodiment, the diameter of the molding is reduced in step b) by cylindrical grinding between centres.

In another preferred embodiment, the diameter of the molding is reduced in step b) on a lathe by turning between centres.

In a preferred embodiment, the diameter of the molding is reduced stepwise in step b) by a total of 0.1 to 3 mm.

In a preferred embodiment, a monolithic molding produced by a sol-gel process is provided in step a).

In a preferred embodiment, a monolithic molding having a diameter of between 4 and 8 mm is employed in step a).

The present invention also relates to a monolithic separating column produced by the process according to the invention.

The present invention furthermore relates to the use of a monolithic separating column according to the invention for the chromatographic separation of at least two substances, as support material in catalytic processes or flow syntheses or in solid-phase extraction.

The moldings employed in the process according to the invention are moldings which have inhomogeneous peripheral regions, in particular those which have been produced in a mold, the so-called gelling mold. This gelling mold determines the size and shape of the monolithic molding to be produced. The term "gelling mold" here is used independently of the production process employed, i.e. irrespective of whether the molding is produced, for example, by a sol-gel process, other polycondensation or polymerization processes or, for example, by sintering. For example, if the gelling mold for the production of columnar moldings is typically a tube, which can be sealed on one or both sides.

Moldings having inhomogeneous peripheral regions are moldings whose outer layer is inhomogeneous or has a different structure to the regions in the interior of the molding. Inhomogeneous peripheral regions may arise, for example, due to the production of the molding (for example as explained above in the case of production in a gelling mold) or due to subsequent treatment of the molding (for example thermal or mechanical treatment).

In accordance with the invention, a monolithic separating column is a porous monolithic molding produced by the process according to the invention by grinding off the outer layer. The monolithic separating column according to the invention can be employed, as described below, for chromatographic or other purposes.

The "outer layer" of a molding is the outer lateral surface or the peripheral region of the molding. During production of the molding, this outer layer is in direct contact with or in close proximity to the gelling mold.

Figure 2:
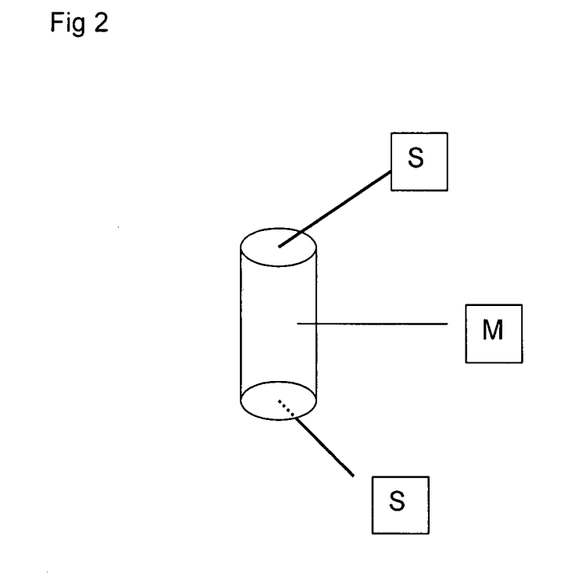
FIG. 2 shows a cylindrical molding with the two end faces S and the lateral surface M.

In accordance with the invention, a porous monolithic molding is a molding having a mono-, bi- or oligomodal pore structure. The pore volume is typically 50 to 80% of the volume of the molding. Preferred moldings have a monomodal pore structure with macropores or particularly preferably a bimodal or trimodal pore structure with meso- and macropores. The interconnected macropores preferably have a diameter which has a median value of greater than 0.1 μm. The diameter of the mesopores preferably has a median value between 2 and 100 nm. Since the moldings treated in accordance with the invention are preferably employed for chromatographic purposes, their dimensions generally correspond to the dimensions which are usual for monolithic chromatography columns. These are typically diameters between 2 and 25 mm and lengths between 2 cm and 1 m. Depending on the area of application of the separating column, however, deviations from these dimensions are possible. The moldings are preferably cylindrical, i.e., columnar, with circular end faces S and a lateral surface M (see FIG. 2), but may also have different shapes for certain applications. Examples are conical columns, columns having polygonal end faces or cuboid moldings.

The moldings may comprise, or consist of all rigid, porous materials which are suitable for the formation of a stable molding, in particular they may comprise, or consist of inorganic, organic or organic/inorganic hybrid materials.

Examples of inorganic materials are silica materials or materials made from other metal oxides, such as, for example, aluminium oxides or titanium oxides, or mixtures of metal oxides.

Examples of organic/inorganic hybrid materials are materials which comprise or consist of a homogeneous three-dimensional network having an organic/inorganic hybrid structure or inorganic materials which are coated with at least one layer of an organic polymer (including in the pores) or organic materials which are coated with at least one layer of an inorganic polymer (including in the pores).

Examples of organic polymers are, in particular, highly crosslinked poly-(meth)acrylic acid derivatives, polystyrene derivatives, polyesters, polyamides, polyethylenes or porous carbon materials.

In a preferred embodiment, the moldings employed in accordance with the invention comprise or consist of inorganic materials, in particular silica materials, or inorganic/organic hybrid materials, in particular materials prepared from organoalkoxysilanes or from mixtures of organoalkoxysilanes and alkoxysilanes prepared in a sol-gel process.

Processes for the production of the moldings from inorganic, organic or organic/inorganic hybrid materials are known to the person skilled in the art. Some of the known processes are explained briefly below by way of example:

In a preferred embodiment, use is made in accordance with the invention of moldings produced by a sol-gel process. Processes of this type are described, for example, in EP 0 710 219 B1 or preferably WO 98/29350. In sol-gel processes, firstly polymerizable low-molecular-weight species are generated and finally aggregated or polymerized materials are obtained via polymerization or polycondensation reactions. The sol-gel method is suitable, inter alia, for use in the hydrolysis of metal alkoxides, metal chlorides, metal salts or combination compounds, which generally contain carboxyl or beta-diketone ligands. A corresponding process is also described in EP 0 363 697.

Suitable alkoxysilanes for the preparation of silica materials which are suitable in accordance with the invention by a sol-gel process are tetraalkoxysilanes $(RO)_4Si$, where R is typically an alkyl, alkenyl or aryl radical, such as C1 to C20 alkyl, C2 to C20 alkenyl or C5 to C20 aryl, preferably a C1 to C8 alkyl radical. Particular preference is given to tetraethoxy- and in particular tetramethoxysilane. The tetraalkoxysilane may equally contain different alkyl radicals (R).

In another embodiment, organoalkoxysilanes or mixtures of organoalkoxysilanes with tetraalkoxysilanes can also be employed instead of an alkoxysilane or mixtures of two or more alkoxysilanes. In this way, inorganic/organic hybrid materials are formed. Suitable organoalkoxysilanes are those in which one to three, preferably one, alkoxy groups of a tetraalkoxysilane have been replaced by organic radicals, such as, preferably, C1 to C20 alkyl, C2 to C20 alkenyl or C5 to C20 aryl. Further organoalkoxysilanes are disclosed, for example, in WO 03/014450 or U.S. Pat. No. 4,017,528.

Instead of in their monomeric form, the alkoxysilanes or organoalkoxysilanes may also be employed in prepolymerized form as, for example, oligomers.

In a sol-gel process, a gel body is built up by hydrolysis of the starting materials, such as, for example, the alkoxysilanes and/or organoalkoxysilanes, in the presence of a pore-forming phase, for example an aqueous solution of an organic polymer. The gel is then aged, and finally the pore-forming substance is separated off. Depending on the type of monomers and any pore formers employed, the specific way in which the process is carried out can vary.

In the case of the use of organoalkoxysilanes, the formation of the pores can be influenced in various ways, for example depending on what pore distribution the monolithic molding is to have.

For example, the addition of a porogen, such as, for example, polyethylene glycol, can optionally be omitted since some organoalkoxysilanes themselves effect the formation of macroporous structures in the molding due to the organic, non-hydrolysable radicals.

If mesopores are additionally desired, a detergent can be added (for example cationic detergents, such as CTAB ($CH_3(CH_2)_{15}N^+(CH_3)_3Br^-$), nonionic detergents, such as PEG (polyethylene glycol), Brij 56 ($CH_3(CH_2)_{15}$—($OCH_2CH_2)_{10}$—OH), Brij 58 ($CH_3(CH_2)_{15}$—($OCH_2CH_2)_{20}$—OH) and TRITON® X detergents ($(CH_3)_3CCH_2CH(CH_3)$—$C_6H_4O$—$(CH_2CH_2O)_xH$ where x=8 (TX-114) or x=10 (TX-100), or block copolymers, such as PLURONIC® P-123 $(EO)_{20}$(propylene oxide, $PO)_{70}(EO)_{20}$ or TWEEN® 85 (polyoxyethylene sorbitan trioleate)), or alternatively an ageing process can be carried out, as disclosed, for example, in WO 95/03256 and in particular in WO 98/29350 (addition of a thermally decomposable substance, such as urea).

A calcination step is frequently typically carried out after the gelling and ageing of the gel. This removes all organic compounds or residues remaining in the molding. Even in the case of the use of organoalkoxysilanes in the monomer sol, calcination can be carried out in the final synthesis step, so that the organic residues are removed from the molding and a completely inorganic molding is obtained. In particular in the case of the use of organoalkoxysilanes having bulky organic radicals, this can be utilised in order to produce pores. The calcination is generally carried out at temperatures between 300 and 600° C.

However, it is equally possible to omit the calcination step or alternatively to select the temperature so that the organic radicals are not attacked, in particular in the case of the use of organoalkoxysilanes. In this way, it is possible to influence the material properties of the moldings, for example with respect to their chromatographic separation properties, through the organic radicals. The temperatures in this case are typically between 100 and 300° C.

It is important for the production of corresponding columns that the pores are uniformly, but also homogeneously distributed throughout the volume of the monoliths produced. Suitable pore-forming chemical substances may be, for example, water-soluble organic polymers, such as polyethylene oxide, or mixtures consisting of a polyalcohol and formamide. It is also possible to use mixtures which comprise formamide and a polyalcohol, such as ethylene glycol, glycerol or sorbitol, as constituents of the pore-forming phase.

If silicon alkoxides are used as organometallic compound, the hydrolysis is preferably carried out in acidic medium. To this end, use is preferably made of dilute acids, to be precise acetic acid or nitric acid in concentrations of 1 mmol/l to 2 mol/l. However, other dilute acids can also be used for this purpose.

The structure of moldings produced by the sol-gel process depends on the selected process parameters and is determined, for example, by the starting materials employed, reaction temperature, pH, nature of any catalyst employed, the amount and molecular weight of the organic polymer used and the solvents used. However, it has been found that reproducible structures are obtained under precisely identical conditions.

The moldings produced in accordance with EP 0 710 219 B1 or preferably WO 98/29350 preferably have structures in which the interconnected macropores, depending on the selected process parameters, have on average diameters in the range from 0.1 to 50 μm, preferably from 0.2 to 20 μm. In particular, the parameters are selected so that moldings having macropore diameters in the range from 0.2 to 10 μm are obtained.

The pore volume arising in the column produced is preferably set in such a way that it is about 50 to 80%, based on the total volume, so that the column has adequate stability for the subsequent grinding treatment and suitable pressure conditions are able to build up during later use.

As already mentioned above, mesopores are additionally located in the walls of the macropores in the case of the preferred materials. The mesopores have average diameters in the range from 2 to 100 nm. Columns whose mesopores have average diameters in the range from 2 to 50 nm, in particular from 5 to 30 nm, have particularly good properties.

The ratio of the mesopore volume to the total volume of the pores should if possible be greater than 10%.

As known for chromatography columns, the moldings employed in accordance with the invention or the separating columns may also be derivatised by functional groups, so-called separation effectors, by bonding these to the surface of the pores, or by supporting biomolecules, for example enzymes, such as glucose isomerase, or metal catalysts, such as platinum or palladium, in the pores. The various separation effectors, such as, for example, ionic, hydrophobic, chelating or chiral groups, and methods for the introduction thereof are known to the person skilled in the art. Examples are given, for example, in WO 98/29350.

Suitable organic moldings can be produced by polymerization processes, for example by free-radical, ionic or thermal polymerization. They must be produced with such a high degree of crosslinking that they are sufficiently rigid not to be unintentionally deformed or damaged by the grinding according to the invention. Furthermore, organic polymer moldings can be produced by bulk polymerization of monomers in a molding, a so-called matrix molding as gelling mold, and subsequent removal of the matrix molding by dissolution.

The matrix moldings, i.e. gelling molds, used for this are typically appropriately dimensioned porous moldings made from silica gel whose pore system is formed, in particular, by macropores. The moldings preferably additionally also have mesopores in the walls of the macropores. The interconnected macropores typically have a diameter which has a median value greater than 0.1 µm. The diameter of the mesopores generally has a median value between 2 and 100 nm. The porosity and specific surface area of the molding polymerized in can be influenced by the type of porosity or the specific surface area of the matrix molding. The resultant moldings according to the invention may accordingly have macropores and preferably also mesopores of the same dimensions as mentioned for the matrix moldings.

Instead of a porous molding, the matrix molding used may also be a column or a corresponding holder which is filled with porous particles. In this case, the particle interspaces usually form macropores.

The matrix moldings used are typically appropriately dimensioned porous moldings whose pore system is formed, in particular, by macropores. The moldings preferably additionally have mesopores in the walls of the macropores. The interconnected macropores typically have a diameter which has a median value greater than 0.1 µm. The diameter of the mesopores generally has a median value between 2 and 100 nm. The porosity and specific surface area of the molding polymerized in can be controlled by the type of porosity or the specific surface area of the matrix molding, with the consequence that the organic moldings formed have macropores and mesopores of the same dimensions as mentioned for the matrix moldings.

Instead of a porous molding, the matrix molding used may also be a column or a corresponding holder which is filled with porous particles. In this case, the particle interspaces usually form macropores.

In order to be able to remove the matrix molding after polymerization is complete, it must be dissolved and washed out without destroying the organic polymer formed. Suitable matrix moldings comprise or consist of inorganic materials, such as inorganic oxides, in particular silica gel. These may be monolithic moldings, as described in WO 94/19 687, WO 95/03 256 or WO 98/29350. They can be employed in calcined or uncalcined form, depending on the desired porosity of the organic polymer to be prepared.

Matrix moldings made from silica gel can be washed out with aqueous bases or with aqueous hydrofluoric acid. If the polymerized-in organic moldings are likewise labile under these conditions, another matrix molding must be selected. This can be, for example, a porous matrix molding made from an organic polymer which is washed out under conditions which do not destroy the polymerized-in molding. Thus, for example, polylactides or melamine-phenol-formaldehyde resins can be employed.

A very wide variety of organic polymeric moldings, which are produced, for example, by free-radical, ionic or thermal polymerization, can be produced in this way. Accordingly, the moldings obtained can comprise or consist of poly(meth)-acrylic acid derivatives, polystyrene derivatives, polyesters, polyamides or polyethylenes. The monomers to be employed for the production are known to the person skilled in the art in the area of organic polymers. Examples thereof are monoethylenically or polyethylenically unsaturated monomers, such as vinyl monomers, vinylaromatic and vinylaliphatic monomers, such as, for example, styrene and substituted styrenes, vinyl acetates or vinyl propionates, acrylic monomers, such as methacrylates and other alkyl acrylates, ethoxy methacrylate and higher analogues, and the corresponding methacrylates or amides thereof, such as acrylamide, or acrylonitrile. Further monoethylenically and polyethylenically unsaturated monomers are given, for example, in EP 0 366 252 or U.S. Pat. No. 5,858,296.

The person skilled in the art is able to combine different monomers in a targeted manner, if desired to add a suitable free-radical initiator and thus to prepare a monomer solution with which the matrix molding can be filled. The polymerization duration and temperature should be matched to the respective monomer solution in accordance with conventional rules.

After completion of the polymerization, the solid molding formed, which consists, for example, of the inorganic matrix polymer and the molded organic polymer, is removed, and the material of the matrix molding is dissolved out. To this end, the molding is placed in a wash solution, optionally with heating, and swirled if necessary. Treatment with aqueous hydrofluoric acid for removal of silica gel typically takes 48 h.

After further washing steps for removal of the aggressive wash solution and final particles, the porous organic polymeric molding is obtained as a cast of the matrix molding employed.

Depending on the desired separation properties, further modifications may also be desirable in the case of moldings made from organic polymers. If the column is to be employed, for example, for affinity or ion-exchange chromatography, the pore surface is desirably covered with corresponding separation effectors if suitable substances have not already been added to the monomer solution and thus introduced directly into the polymer. Preferably, however, the functionalisation is only carried out subsequently, either directly with corresponding separation effectors or by introduction of functional groups, which can then be reacted with separation effectors. Further modifications may also be introduced by block or graft polymerizations on the polymeric moldings. Separation effectors and monomers which contain further functionalities, such as, for example, oxirane rings, in addition to a polymerizable double bond are known to the person skilled in the art. Examples are given in WO 96/22316 or WO 95/10354.

It is equally possible to use suitable functionalities of the moldings according to the invention for binding or immobilisation of biomolecules, such as, for example, enzymes.

Furthermore, moldings having particular separation properties can be produced. In the production of a molding with the aid of a matrix molding as gelling mold, template molecules can, as in "molecular imprinting", be bonded to the surface of the, in this case porous or nonporous, matrix molding. The interspaces or pores are subsequently filled with monomer solution and polymerized to completion. During the polymerization, cavities form which surround the template molecules. The matrix molding and the template molecules bonded thereto are then washed out. This has the advantage that the bonding to the matrix molding causes the template molecules to adopt a position aligned in a defined manner. Cavities which are more precisely defined thus form which are able to enter into clearer and stronger interactions during chromatographic separation. After the polymerization, all template molecules can be washed out. The monomer solution is only added and polymerized in the second step.

Since the polymeric organic moldings are generally produced using gelling molds, for example in the form of tubes or suitable inorganic or organic moldings as matrix moldings, they, like the inorganic or inorganic/organic, monolithic separating columns described above, have inhomogeneous peripheral regions which impair the separation efficiency. As is also the case in the inorganic or inorganic/organic moldings, the influence of the peripheral regions becomes greater, the smaller the diameter of the column produced.

Surprisingly, it has now been found that it is possible to improve the separation efficiency of rigid moldings for use in liquid chromatography. This is achieved by uniformly removing material from the peripheral regions of the molding by a grinding process. In this way, the diameter of the moldings is reduced. Depending on the type of grinding process, the diameter can be reduced in one step or preferably stepwise. Layer thicknesses of 5 μm to 100 μm are typically removed per grinding step, with the lower limit generally being determined by the respective grinding process or the machine employed and the upper limit by the material. If it is attempted, for example in the case of an inorganic silica monolith having a porosity of about 80%, to grind off excessively thick layers (>100 μm), fractures in the molding occur more frequently, which then make the use of the molding as chromatography column impossible.

The total layer thickness removed after grinding-off one or more times depends on the diameter of the molding employed and the desired diameter of the later separating column. In order to effectively eliminate interfering marginal effects, which result, for example, from the molding production process, the diameter should be reduced by a total of at least 5 μm, preferably by 20 μm. A reduction by 20 μm to 4 mm, preferably by 0.02 mm to 3 mm, is typical. The process according to the invention can be employed particularly advantageously for the production of separating columns having a diameter of less than 6 mm, preferably less than 4 mm. To this end, moldings having an initial diameter of between 4 and 8 mm are generally employed. A uniform layer is preferably removed, i.e. the thickness of the layer removed is equal everywhere (over the entire circumference of the molding). However, it is also possible to remove layers of non-uniform thickness, i.e., for example, a thicker layer on one side of the lateral surface.

Particular preference is given in accordance with the invention to a centreless grinding process, in which the diameter of the moldings is reduced stepwise by a few tenths of a millimeter in each case with the aid of rotating grinding wheels. According to common experience, the person skilled in the art would now assume that removed material liberated during this process would act, during the grinding process, on the peripheral regions of the separating columns treated in this way and adversely affect the outer pore structure. However, it has now been found that monolithic separating columns produced in accordance with the invention give significantly better chromatographic separation results compared with separating columns which have been produced by conventional methods directly by the sol-gel process with the desired small diameter.

Figure 1:
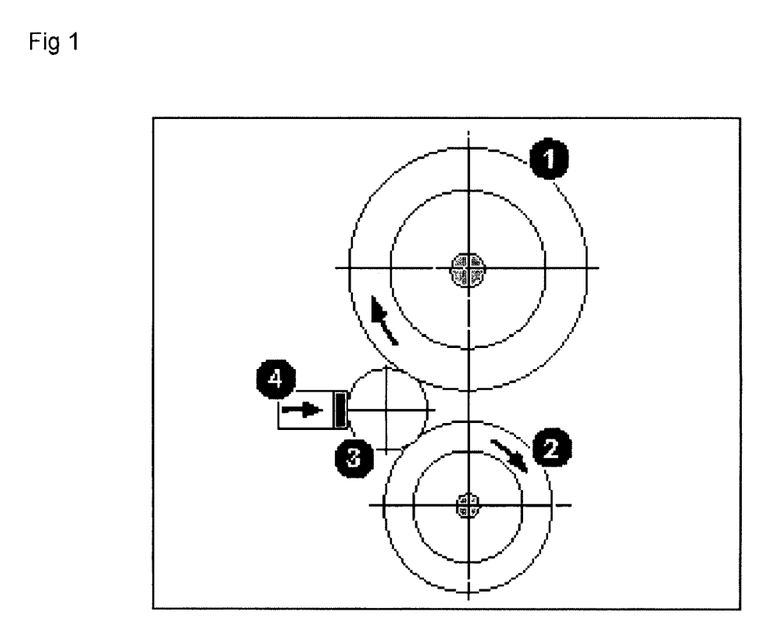
FIG. 1 shows diagrammatically the basic principle of "centreless grinding".

The actual grinding process is preferably carried out on a grinding machine which has a grinding wheel (1) and a regulating wheel (2), by means of which the workpiece (3) is rotated, and an input carriage or feed carriage (4), where the latter can be introduced during the grinding process into the gap which forms between the rotating grinding wheel (1) and the counter rotating regulating wheel (2). The workpiece (3) is held by the feed carriage (4) during the grinding. The width of the gap between grinding wheel (1) and regulating wheel (2) can be regulated very finely. This enables workpieces positioned in the gap by means of the feed carriage (4) to be ground to an accuracy of nm.

During the grinding, the grinding wheel (1) rotates more quickly than the regulating wheel. Since the workpiece (3) on the feed carriage (4) is rotated by the regulating wheel (2), it in turn rotates more slowly than the grinding wheel (1). This results in removal of material. Centreless grinding thus means that there is no holder at the ends of the workpiece. The basic principle of "centreless grinding" is shown diagrammatically in FIG. 1. In order to prevent extremely fine, ground-off material particles coming into contact again with the monolith to be treated as workpiece, a suction device is installed above the gap between grinding wheel (1) and regulating wheel (2). During the grinding, the suction device produces a constant stream of air, immediately removing mobile fine particles that have been removed. In addition, a further suction device is installed above the surface of the grinding wheel in the opposite position to the fed workpiece and continuously sucks adhering particles off the surface of the grinding wheel (1). In this way, finely particulate material removed from the monoliths to be treated can successfully be prevented from reaching the surface of the workpiece again and disadvantageously interacting with the exposed pores. By suitable regulation of the ratio of the rotary speeds of the grinding wheel (1) and the regulating wheel (2) to one another, it is possible in a simple manner to remove extremely thin layers from the outer surface of the molding without damaging the pore structure and running the risk of irregularly small areas being damaged or broken out of the surface.

The removal of ground off material may be achieved by other methods than a suction device, e.g., a blowing device, etc.

During the grinding process, the molding as workpiece is fed continuously through the gap with the feed carriage (4), with the molding lying on the feed carriage in a freely rotatable manner. A precisely adjustable holder on the feed carriage ensures that the monolith is delivered to the grinding site and ground uniformly over the entire length. At the same time, breaking of the molding is prevented since it lies in the feed carriage over the entire length.

In order to obtain good grinding results, it is advisable, for example, to grind a monolithic molding produced by the sol-gel process to the desired small diameter in a plurality of steps and to remove layers with a maximum thickness of a few μm in each case. According to experience, better grinding results are achieved the thinner the ground-off layers are.

Further experiments have shown, in a surprising manner, that it is not only by the centreless grinding process described that interfering outer peripheral regions can be removed and the diameter of the monolithic separating columns thus reduced, but instead that other grinding methods can give a corresponding result if very thin layers are removed under suitable feed conditions preferably in a plurality of steps from the outside of the monolithic separating columns produced. It is important in each case here that an extremely low pressure is used and the molding is supported uniformly over the entire length, so that lever forces, which would result in breaking of the monolith, cannot act. In addition, it is advantageous, irrespective of the grinding process used, to remove particles formed during the grinding as soon as possible after formation from the surface of the treated molding by suction and thus to prevent settling in the outer pores.

In accordance with the invention, the reduction in the diameter of a corresponding monolithic molding can thus be carried out in an appropriately equipped cylindrical grinding machine which allows extremely fine setting by cylindrical grinding between centres.

Taking into account the sensitive structure of the monolithic moldings, another possibility is to remove thin outer layers by turning between centres using a lathe and in this way to produce in accordance with the invention separating columns having properties which are identical over the entire cross section.

Turning is a material-removal process using a geometrically determined cutting edge. In general, the turning movement is carried out by the workpiece, in our case by the turning movement of the monolith. The monolith is firmly clamped here and is moved along the surface to be machined and rotated at the same time. Lathes which are suitable for this purpose are commercially available and can be fitted with suitable holding and suction devices by the person skilled in the art.

In addition, it has been found that all methods for reducing the diameter by removal of extremely thin outer layers of the monolith are suitable per se for the production of monolithic separating columns according to the invention having improved separation properties from organic or inorganic monolithic moldings crosslinked in a stable manner or moldings made from hybrid materials.

In this sense, it is also possible to employ methods for core hole drilling, where the workpiece, here a monolith, is machined in an annular manner and, besides the bore hole, a cylindrical core, here the organic or inorganic monolithic separating column of reduced diameter, remains. This has the advantage that the starting workpiece used can be a corresponding molding having dimensions which simplify handling. However, it is also advantageous in this case for the original diameter to differ from the desired diameter by only a few mm.

It is furthermore possible to remove thin outer layers using abrasive paper, either manually or by means of corresponding equipment. In this case too, it is advantageous to carry out the sanding with removal of the removed material by suction. For this purpose, thin layers are removed successively using different grades of abrasive media, starting with the coarsest grade. It goes without saying that, as in all methods described above, the work must be carried out extremely sensitively and the workpiece to be treated must be reliably bedded on a support.

This operation can also be carried out mechanically using a belt grinder if the latter has a suitable holding device for the moldings to be treated and is provided with a suction system.

When the grinding operation is complete, it is advisable, irrespective of the grinding method, to wash the resultant monolithic column again in a suitable solvent, such as, for example, water, alcohol, ether or the like, and to free it from any particles still adhering.

After the grinding, a ready-to-use chromatography column can be produced from the resultant blank by cladding. The cladding can be carried out by known methods. Suitable holders and claddings are known for inorganic monolithic sorbents from, for example, WO 98/59238 and WO 01/03797. Suitable plastic claddings can comprise or consist of, for example, PEEK or fibre-reinforced PEEK.

In accordance with the invention, the term "cladding" denotes any type of processing by means of which a porous monolithic molding can be sealed off in a liquid-tight manner in such a way that liquid can only flow through from one of the end faces without the liquid exiting from the lateral side of, for example, the cylinder. Instead, the entire flow is through the molding in a longitudinal direction, and the liquid exits again at the other end face. Furthermore, the cladding should have the smallest possible dead volume, in particular for chromatographic purposes. This means that the cladding should be in closest possible contact with the lateral side of the molding.

Accordingly, a cladding is, for example, a pressure holder into which the molding can be clamped, a pressure shell, a cartridge holder or a conventional column cladding of, for example, metal or preferably plastic, which can be shrunk, for example, onto the molding or into which the molding can be cast or sintered.

Cladding with a particularly small dead volume, as described in WO 01/77660 A1, is particularly advantageous. According to this process, thin tubes having a correspondingly small internal diameter are produced in a first step from suitable plastics, to which fibre materials are optionally added, by extrusion or injection molding. The ground monolithic chromatography columns are subsequently introduced into these thin tubes. The respective tube is then brought into closest possible contact with the molding by warming and shrinking, producing a cladding with a small dead volume. Only materials having a suitable viscosity can be attached sufficiently tightly to the molding. The use of homogeneous tubes which have a uniform wall thickness over the entire length is advantageous in this step. The patent application in WO 01/77660 A1 describes both plastic compositions which are suitable for this purpose and processes for the production of the claddings. A corresponding procedure can also be used here. However, methods of cladding other than those described here can also be employed. It is important for a good separation behaviour, irrespective of the cladding method, that the formation of dead volumes, which would adversely affect the separation behaviour of the columns, is suppressed.

After the clad chromatography columns of reduced diameter have been provided with suitable connectors, filters, seals, etc., they can be employed in the desired, in particular chromatographic, application.

Furthermore, the moldings according to the invention can also be employed, with or without cladding, for other purposes, such as, for example, as catalyst support in catalytic processes, as catalyst or co-reactant in flow syntheses or for solid-phase extraction or solid-phase microextraction.

The process according to the invention offers for the first time the possibility of eliminating inhomogeneities in the peripheral regions of the lateral surface, which arise, in particular, through the production in a gelling mold, in a simple and effective manner. Surprisingly, the lateral surface is not changed by the grinding in such a way that worse separation efficiencies arise on use in chromatography. Indeed, the separation efficiency of a ground column is improved.

Investigations of the monolithic separating columns produced in accordance with the invention have shown that they have homogeneous physical properties over the entire cross section and the entire length. It has been found that, even after cladding, the outer pores have retained their structure. They are adversely affected neither by the grinding operation nor by the cladding process.

The clad monolithic chromatography columns according to the invention exhibit excellent separation properties. Even after storage in solvents and frequent use, no or only slight impairment of the separation efficiencies is evident. The process according to the invention thus ensures, in particular, the production of chromatography columns for the separation of relatively small amounts of liquid.

In order to carry out the present invention, further details are revealed in the examples given below.

Even without further comments, it is assumed that a person skilled in the art will be able to utilise and carry out the present invention in the broadest scope with reference to the above description and the examples given.

For better understanding and in order to illustrate the invention, examples which are within the scope of protection of the present invention are given below by way of supplement. These preferred specific embodiments are only illustrative and are not suitable for restricting the present invention thereto.

The complete disclosure content of all applications and publications mentioned in this application is, in addition, hereby incorporated into this application by way of reference.

EXAMPLES

Example 1

Production of a Monolithic Molding

In a first step, 0.70 g of polyethylene oxide (Article No. 85645-2 from Aldrich, molecular weight: 10,000) is dissolved in a 0.001 mol/l aqueous acetic acid solution. 5 ml of tetramethoxysilane are mixed with this solution with stirring in order to effect a hydrolysis reaction. After stirring for a few minutes, the clear reaction solution formed is transferred into a suitable, sealable vessel and held at a constant temperature of 40° C. The reaction solution solidifies after about 40 minutes.

The solidified product is left to stand at constant temperature for a few hours. It is subsequently immersed in an aqueous 0.1 molar ammonia solution at 40° C. for three days, during which the solution is continuously replaced little by little. The pH of the ammonia solution here is about 10. After this treatment, the resultant gel is dried at 60° C. and then heated to a temperature of 600° C. The heating is carried out so slowly that the temperature increases by a maximum of 100° C. per hour. In this way, amorphous silica gel or a silica monolith is formed from the porous material.

It can be shown by electron-microscopic studies that a product having uniform, interconnected macropores having a size of about 1.6 μm (1600 nm) has been produced. In addition, it can be shown by nitrogen adsorption that relatively small pores, so-called mesopores, having a diameter of about 10 nm are present in the macropores.

The size of the mesopores can be influenced by variation of the temperature during replacement of the acetic acid solution by ammonia solution, that is by setting the temperature to a value between 25 and 60° C. while the other production conditions remain unchanged. While the macropores remain unchanged, the size of the mesopores can be varied in the range from 6 to 13 nm in this way. The higher the temperature selected during the solvent exchange, the larger the mesopores that form.

Example 2

3 silica monoliths having a diameter of 7.2 mm and a length of about 14.5 cm, produced as described in Example 1, are reduced to a diameter of 4.6 mm by means of centreless cylindrical grinding in a plurality of grinding steps.

The monolithic columns obtained in this way are introduced into a PEEK tube over which a Teflon shrink sleeve is also pulled. (The cladding is carried out by a known process, as described in EP 1269179 A1, with a solvent- and mechanically stable polymer). The resultant product is subsequently heated to about 400° C. in an oven. After removal from the oven, the Teflon sleeve is shrunk by cooling. In the process, the molten PEEK is forced onto the silica gel monolith with no dead volumes. The separating columns are then investigated by chromatography in the adsorption system with heptane/dioxane (95/5; v/v) and 2-nitroanisole.

The following separation efficiencies and peak symmetries were obtained.

|  | Separation efficiency N/m | Peak symmetry Tusp |
| --- | --- | --- |
| Column 1 | 120520 | 1.03 |
| Column 2 | 127070 | 0.97 |
| Column 3 | 122960 | 1.06 |

Example 3

3 silica monoliths having a diameter of 7.2 mm and a length of 12.5 cm, produced as described in Example 1, are reduced to a diameter of 4.6 mm by means of a centreless cylindrical grinding machine. They are subsequently refluxed for 17 hours in a 20% solution of N,N-diethylaminodimethyloctadecylsilane in toluene and washed with n-heptane in a Soxhlet. After drying, the monoliths are again refluxed for 17 hours in 100% hexamethyldisilazane (HMDS) and re-washed. The derivatised RP-18 monoliths (4.6 mm in diameter) are clad with a solvent- and mechanically stable polymer (as described in Example 2) using existing processes, as disclosed in EP 1269179 A1, and investigated by chromatography in reversed phase mode with acetonitrile/water (60/40; v/v) and anthracene. The following separation efficiencies and peak symmetries were obtained.

|  | Separation efficiency N/m | Peak symmetry Tusp |
| --- | --- | --- |
| Column 1 | 81510 | 1.52 |
| Column 2 | 104930 | 1.57 |
| Column 3 | 86610 | 1.39 |

Example 4

3 silica monoliths having a diameter of 4.6 mm and a length of 12.5 cm, produced as described in Example 1, are reduced to a diameter of 3 mm by means of a centreless cylindrical grinding machine. The monolithic columns obtained in this way were clad with a solvent- and mechanically stable polymer using existing processes, as disclosed in EP 1269179 A1, and investigated by chromatography in the adsorption system with heptane/dioxane (95/5; v/v) and 2-nitroanisole. The following separation efficiencies and peak symmetries were obtained.

|  | Separation efficiency N/m | Peak symmetry Tusp |
| --- | --- | --- |
| Column 1 | 102910 | 1.05 |
| Column 2 | 106290 | 0.99 |
| Column 3 | 111500 | 1.06 |

Comparatively poor separation efficiencies and TUSP values are obtained in the case of silica monoliths produced directly by the process described in Example 1 with a diameter of 3 mm.

Example 5

3 silica monoliths having a diameter of 4.6 mm and a length of 12.5 cm, produced as described in Example 1, are reduced to a diameter of 2 mm by means of a centreless cylindrical grinding machine. The monolithic columns obtained in this way were clad with a solvent- and mechanically stable polymer using existing processes, as disclosed in EP 1269179 A1, and investigated by chromatography in the adsorption system with heptane/dioxane (95/5; v/v) and 2-nitroanisole. The following separation efficiencies and peak symmetries were obtained.

|  | Separation efficiency N/m | Peak symmetry Tusp |
| --- | --- | --- |
| Column 1 | 76170 | 1.08 |
| Column 2 | 66727 | 1.04 |
| Column 3 | 67582 | 1.01 |

The entire disclosures of all applications, patents and publications, cited herein and of corresponding European application No. 06007395.4, filed Apr. 7, 2006, and European application No. 06008141.1, filed Apr. 20, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for preparing a monolithic separating column comprising
a) providing a porous cylindrical monolithic molding, which comprises an inorganic or organic/inorganic hybrid material, which may be coated, having a diameter which has an inhomogeneous peripheral region, with the proviso that the molding is not comprised of organic polymers, and
b) reducing the diameter of the molding by at least 5 µm by grinding off an outer layer one or more times to yield a column having homogeneous properties across over its entire cross section by removing the outer inhomogeneous layer.

2. A process according to claim 1, wherein the diameter of the porous monolithic molding is reduced by at least 20 µm by grinding off an outer layer one or more times.

3. A process according to claim 1, further comprising c) cladding the ground molding in a liquid-tight manner following b).

4. A process according to claim 1, wherein the diameter of the molding is reduced in a centreless grinding process.

5. A process according to claim 1, wherein the diameter of the molding is reduced with the aid of a rotating grinding wheel.

6. A process according to claim 1, wherein the diameter of the molding is reduced by cylindrical grinding between centres.

7. A process according to claim 1, wherein the diameter of the molding is reduced on a lathe by turning between centres.

8. A process according to claim 1, wherein the diameter of the molding is reduced stepwise by a total of 0.1 to 3 mm.

9. A process according to claim 1, wherein the molding provided in step a) is a monolithic molding that has been produced in a gelling mold.

10. A process according to claim 1, wherein the molding provided in step a) is a monolithic molding that has been produced by a sol-gel process.

11. A process according to claim 1, wherein the molding provided in step a) is a monolithic molding having a diameter of 4 to 8 mm.

12. A process according to claim 1, wherein during grinding ground off material is removed so that such ground off material does not contact the surface of the molding.

13. A process according to claim 1, wherein during grinding a suction device removes ground off material.

14. A process according to claim 1, wherein the diameter of the molding after the grinding off of an outer layer one or more times is less than 6 mm.

15. A process according to claim 1, wherein the diameter of the molding after the grinding off of an outer layer one or more times is less than 4 mm.

16. A process according to claim 1, wherein the diameter of the molding after the grinding off of an outer layer one or more times is 2 to 6 mm.

17. A process according to claim 1, wherein the inorganic material is a silica material, a material made from a metal oxide, aluminium oxide, titanium oxide, or a mixture of metal oxides, or wherein the organic/inorganic hybrid material has a homogeneous three-dimensional network having an organic/inorganic hybrid structure or is an inorganic material which is coated with at least one layer of an organic polymer, including in the pores, or is a material prepared from an organoalkoxysilane or from a mixture of an organoalkoxysilane and an alkoxysilane.

18. A process according to claim 1, wherein the molding consists of an inorganic or organic/inorganic hybrid material, which may be coated.

19. A process according to claim 1, wherein the molding consists of an inorganic material.

20. A process according to claim 1, wherein the molding consists of an organic/inorganic hybrid material.

* * * * *